(12) United States Patent
Giaffreda et al.

(10) Patent No.: US 9,687,484 B2
(45) Date of Patent: Jun. 27, 2017

(54) CRYSTALLINE FORMS OF AN ANTIDEPRESSANT COMPOUND

(71) Applicant: DIPHARMA FRANCIS S.r.l., Baranzate (MI) (IT)

(72) Inventors: Stefano Luca Giaffreda, Medicina (IT); Marco Curzi, Medicina (IT); Elena Dichiarante, Medicina (IT); Pietro Allegrini, San Donato Milanese (IT); Renzo Graziosi, Baranzate (IT); Chiara Vladiskovic, Baranzate (IT)

(73) Assignee: Dipharma Francis S.r.l., Baranzate (MI) (IT)

( * ) Notice: Subject to any disclaimer, the term of this patent is extended or adjusted under 35 U.S.C. 154(b) by 0 days.

(21) Appl. No.: 14/791,736

(22) Filed: Jul. 6, 2015

(65) Prior Publication Data

US 2016/0015706 A1 Jan. 21, 2016

(30) Foreign Application Priority Data

Jul. 18, 2014 (IT) .......................... MI2014A001319
Sep. 24, 2014 (IT) .......................... MI2014A001657

(51) Int. Cl.
*A61K 31/495* (2006.01)
*C07D 295/096* (2006.01)

(52) U.S. Cl.
CPC ........ *A61K 31/495* (2013.01); *C07D 295/096* (2013.01)

(58) Field of Classification Search
CPC .......................... A61K 31/495; C07D 295/096
See application file for complete search history.

(56) References Cited

FOREIGN PATENT DOCUMENTS

| IN | 1476/MUM/2014 | | 4/2014 |
|----|---------------|----|--------|
| IN | 3288/MUM/2014 | | 10/2014 |
| WO | 03029232 | A1 | 4/2003 |
| WO | 2007144005 | A1 | 12/2007 |
| WO | 2010094285 | A1 | 8/2010 |
| WO | 2014044721 | A1 | 3/2014 |
| WO | 2015166379 | A2 | 11/2015 |

*Primary Examiner* — Sahar Javanmard
(74) *Attorney, Agent, or Firm* — Rothwell, Figg, Ernst & Manbeck, P.C.

(57) ABSTRACT

The present invention relates to novel crystalline forms of vortioxetine hydrobromide, in particular three crystalline forms, a process for their preparation, a pharmaceutical composition containing said novel crystalline forms, and a process for the purification of vortioxetine or a salt thereof, comprising the formation of one or more of the novel crystalline forms of vortioxetine hydrobromide described herein.

4 Claims, 8 Drawing Sheets

CRYSTALLINE FORMS OF AN ANTIDEPRESSANT COMPOUND

FIELD OF INVENTION

The present invention relates to the hydrobromide salt of 1-[2-(2,4-dimethylphenylsulphanyl)phenyl]piperazine of formula (I), also known as vortioxetine hydrobromide, in three crystalline forms herein defined as λ, ω and σ, a process for their preparation, and a pharmaceutical composition containing said novel crystalline forms. Another subject of the invention is a process for the purification of vortioxetine or a salt thereof comprising the formation of one of the novel crystalline forms of vortioxetine hydrobromide described herein.

PRIOR ART

Vortioxetine, namely 1-[2-(2,4-dimethylphenylsulphanyl)phenyl]piperazine, of formula (I), is an atypical antidepressant that exerts a combined SERT-inhibitor, 5-HT$_3$ antagonist and partial 5-HT$_{1A}$ agonist action.

(I)

Vortioxetine is present on the market as hydrobromide salt, under the trademark Brintellix®.

Vortioxetine as such is known from WO 03/029232 (example 1e).

WO 2007/144005 also discloses various crystalline forms of vortioxetine and its salts, in particular a crystalline form of vortioxetine base, three crystalline forms of vortioxetine hydrobromide (defined as the alpha, beta and gamma crystalline forms), a hemihydrated crystalline form of vortioxetine hydrobromide, and other crystalline forms of vortioxetine salts (hydrochloride, mesylate, fumarate, maleate, meso-tartrate, L-tartrate, D-tartrate, sulphate, phosphate and nitrate).

WO 2007/144005 also clearly specifies that the subject of the invention is crystalline forms of the vortioxetine hydrobromide salt, as they have the ideal characteristics for oral pharmaceutical forms, in particular as tablets. Tablets are often preferred by patients and doctors due to their ease of administration and safety of dose.

Moreover, the preferred compounds of WO 2007/144005 are non-solvated crystalline forms which are poorly hygroscopic.

In any event, the crystalline forms of vortioxetine hydrobromide gamma and hemihydrate, as described and characterised in WO 2007/144005, present significant hygroscopicity, and in particular a high tendency to absorb water, under conditions of greater relative humidity than the standard conditions, and are therefore unsuitable for use in pharmaceutical formulations, as also acknowledged by WO2014/044721 at page 2, last paragraph.

Other solvated crystalline forms of vortioxetine hydrobromide are disclosed in WO 2007/144005 and WO 2010/094285; said crystalline forms are solvated forms containing ethyl acetate or isopropanol. However, it should be noted that as the solvent content in the active ingredients must not exceed specific limits (as expressly regulated by the ICH Guidelines, for example), said solvated crystalline forms are also unsuitable for use in pharmaceutical formulations, but could possibly be used as intermediates in the preparation of other crystalline forms of vortioxetine hydrobromide, such as the form of vortioxetine hydrobromide present in the commercially available product Brintellix®.

Finally, WO 2014/044721 also discloses crystalline forms of vortioxetine hydrobromide, such as anhydrous or hydrated forms (in particular a substantially anhydrous form described as the delta form).

The delta crystalline form disclosed in WO 2014/044721 is said to have improved characteristics, in particular compared with the alpha and beta crystalline forms of WO 2007/144005. The high solubility in water of said delta crystalline form is said to make it more suitable for formulation in the pharmaceutical field, and therefore an alternative crystalline form of vortioxetine hydrobromide to the one present in Brintellix®.

In any event, said delta crystalline form has not proved to be advantageously usable in the preparation of commercially available vortioxetine hydrobromide.

Moreover, the monohydrate crystalline form of vortioxetine hydrobromide, disclosed in WO 2014/044721, though usable in the preparation of the delta form of vortioxetine hydrobromide disclosed in WO 2014/044721, is not an intermediate useful to prepare the crystalline form of the commercially available vortioxetine hydrobromide; moreover, said crystalline form does not appear to have particular characteristics of improved solubility or low hygroscopicity which would make it suitable for use in pharmaceutical formulations.

There is consequently a need to provide novel crystalline forms of vortioxetine hydrobromide that eliminate the above-mentioned drawbacks and are therefore stable, not hygroscopic, particularly soluble in water and biological fluids, with optimum characteristics for formulation in pharmaceutical technology, and also advantageously usable as intermediates for the preparation of vortioxetine base or a salt thereof, in particular the hydrobromide, and crystalline forms of vortioxetine hydrobromide, in particular its commercially available crystalline form.

SUMMARY OF THE INVENTION

Disclosed are three crystalline forms of vortioxetine hydrobromide, hereinafter defined as crystalline forms λ, ω and σ, a process for their preparation, a pharmaceutical composition containing at least one of said crystalline forms λ, ω and σ, and a process for the purification of vortioxetine, or a salt thereof, comprising the formation of a crystalline form λ, ω and/or σ as defined herein.

Crystalline forms λ and σ have been characterised by Bruker D8 Advance X-ray powder diffraction (XRPD), Bragg-Brentano geometry, CuKα radiation with wavelength λ=1.54; scanning with 2θ angle range of 3° to 40°, step size of 0.02° for 0.5 seconds per step. Linear solid-state detector (Lynx Eye).

Crystalline form ω of vortioxetine hydrobromide was characterised by X-ray powder diffraction (XRPD). The X-ray powder diffraction (XRPD) spectra shown in FIGS. 3, 6 and 7 were collected with a PANalytical X'Pert PRO automatic powder diffractometer under the following operating conditions: CuKα radiation (λ=1.54 Å), scanning with a 2θ angle range of 3-40° with a step size of 0.017° for 12.7 sec.

The FTIR spectrum of crystalline form ω was obtained with ThermoFischer Nicolet FTIR 6700 instrumentation, number of scans per sample: 32, number of background scans: 32, resolution: 4.000 cm$^{-1}$, sample gain: 8.0, optical speed: 0.6329, aperture: 100.00, detector: DTGS KBr, beamsplitter: KBr.

The DSC pattern of crystalline form λ was obtained with a differential scanning calorimeter (Mettler Toledo DSC 822e), using STARe software, under the following operating conditions: open aluminium capsule, scanning rate 10° C./min, with nitrogen as purge gas.

The DSC pattern of crystalline form ω was obtained with a DSC 200 F3 Maia differential scanning calorimeter under the following operating conditions: closed aluminium capsule, scanning rate 10° C./min, with nitrogen as purge gas.

The water content of vortioxetine hydrobromide forms λ and ω and σ as defined herein, was calculated by titration using the Karl Fischer technique. Vortioxetine hydrobromide in crystalline form λ, as obtainable according to the present invention, is a hydrated form of vortioxetine hydrobromide.

Vortioxetine hydrobromide in crystalline form ω, as defined herein, is a hydrated, more particularly monohdryate, crystalline form of vortioxetine hydrobromide.

Vortioxetine hydrobromide in crystalline form σ, as defined herein, is an anhydrous crystalline form of vortioxetine hydrobromide.

DETAILED DESCRIPTION OF THE INVENTION

Figure 1:
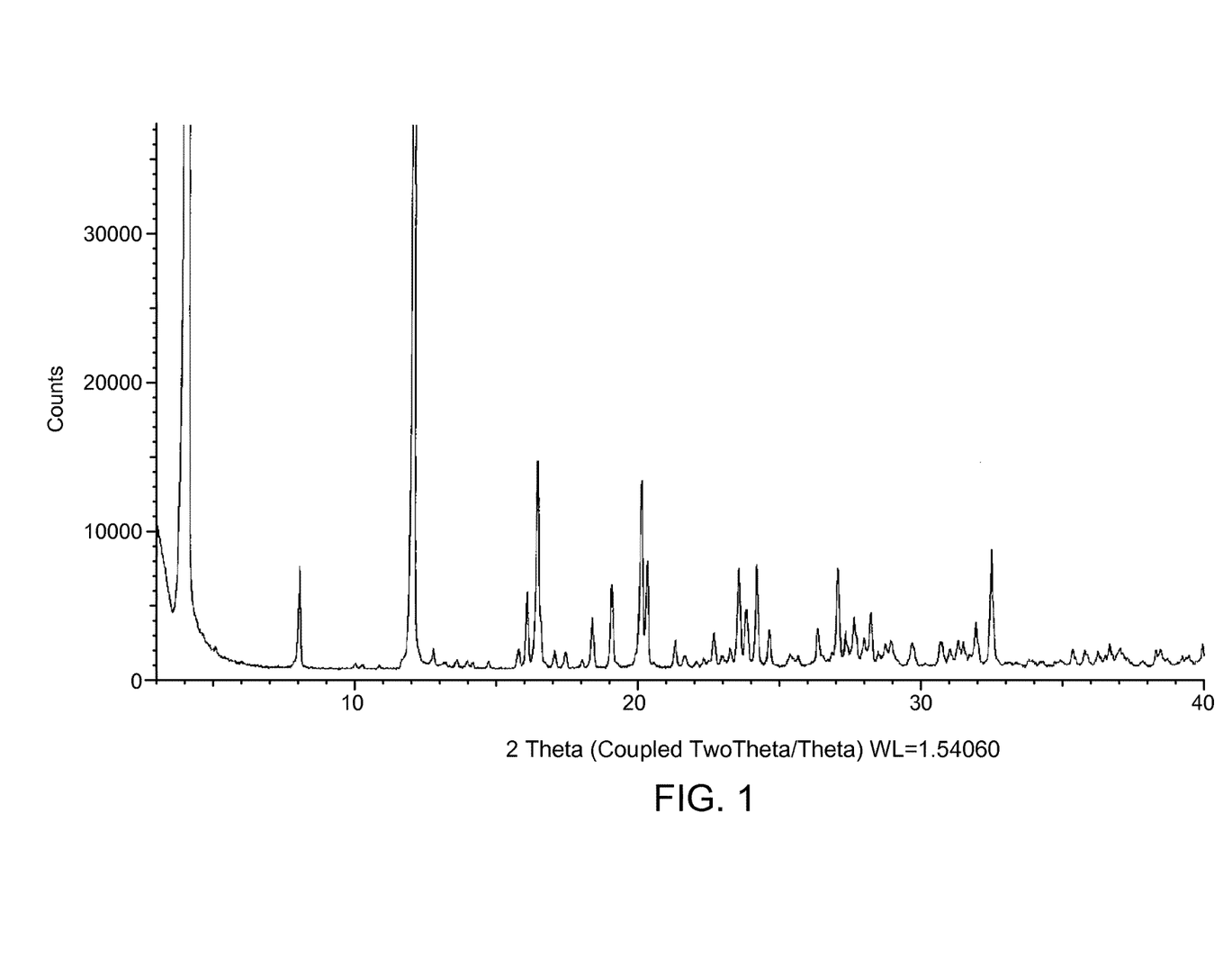
FIG. 1: XRPD spectrum of vortioxetine hydrobromide in crystalline form λ.
Figure 3:
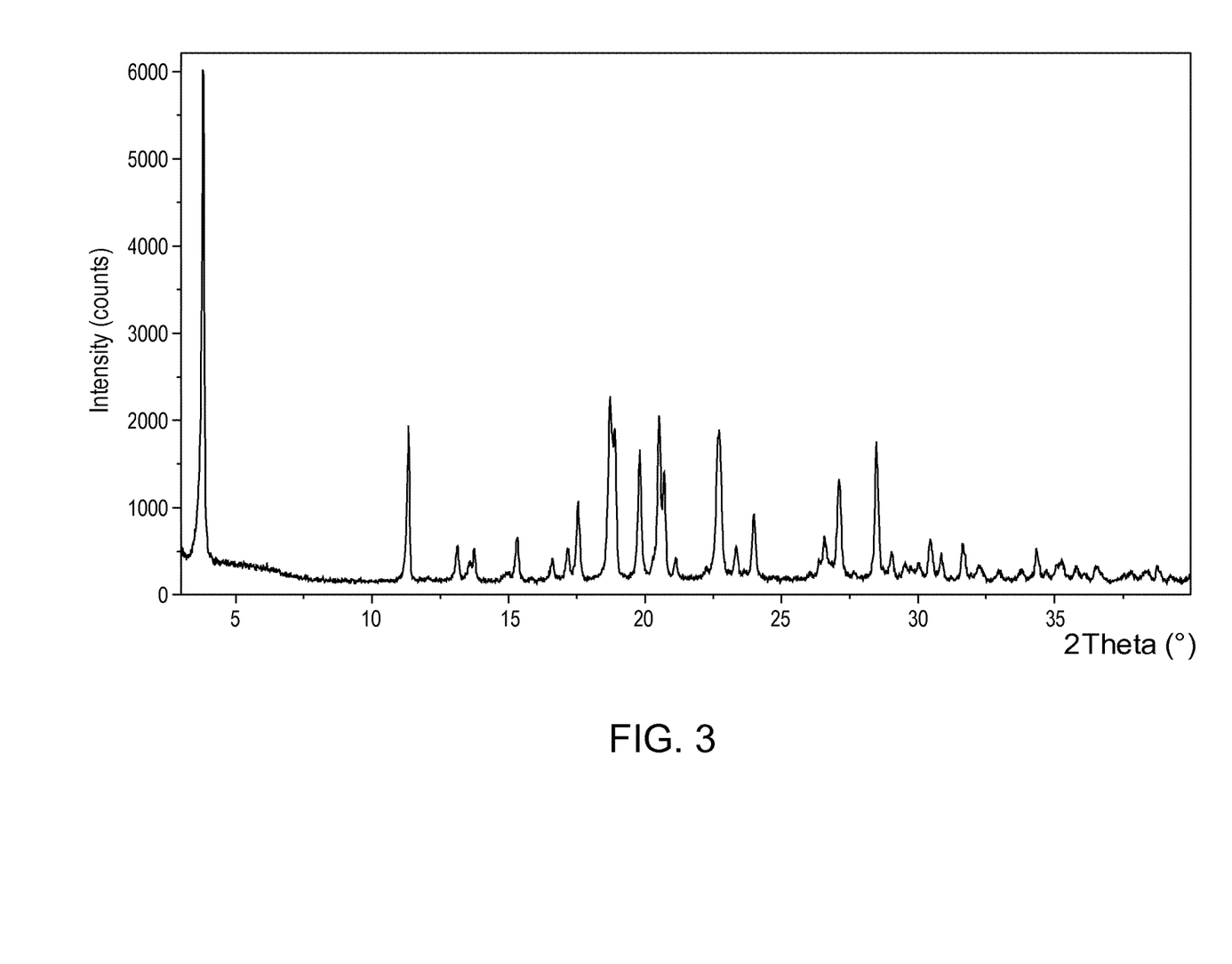
FIG. 3: XRPD spectrum of vortioxetine hydrobromide in crystalline form ω.
Figure 8:
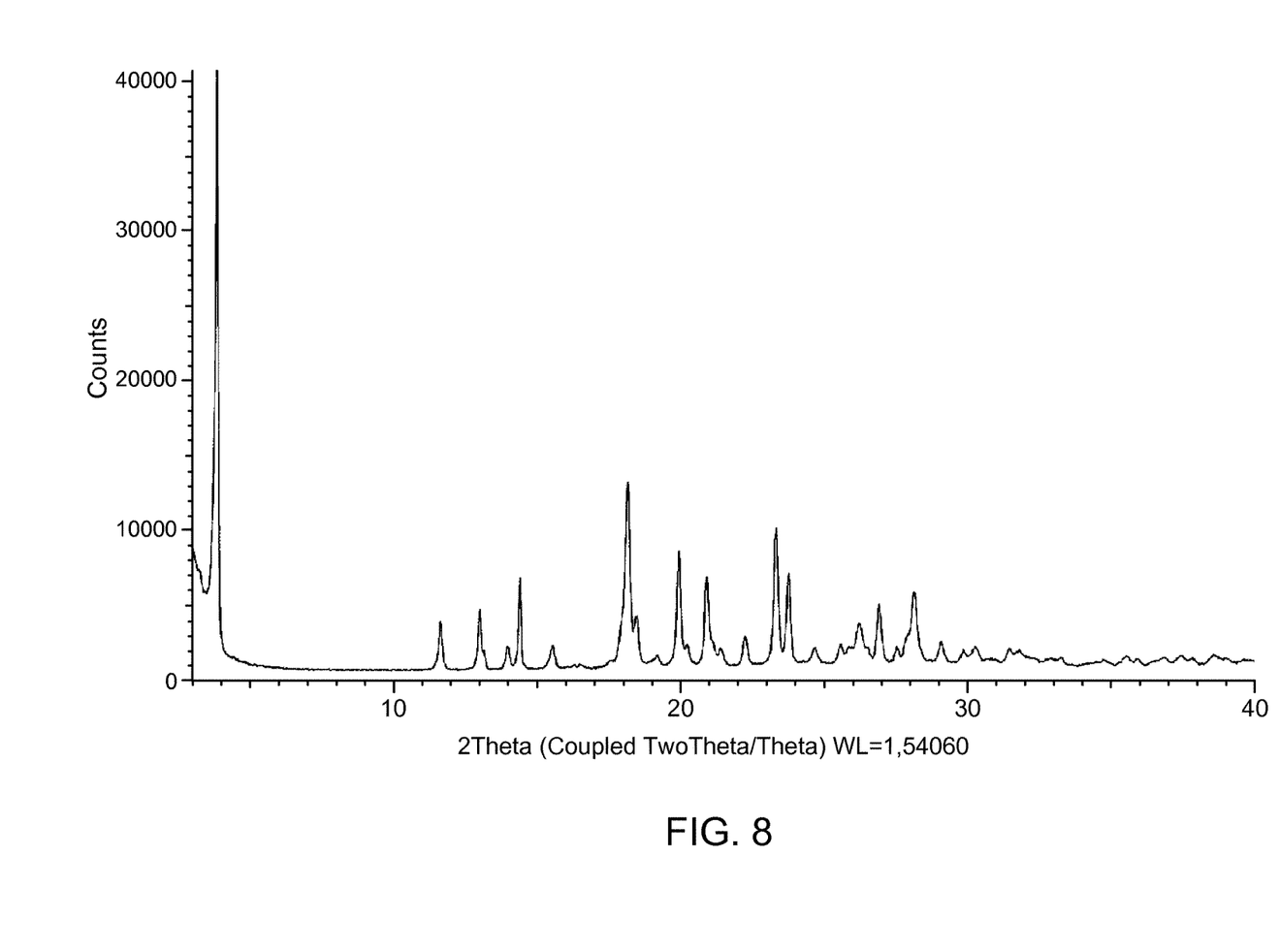
FIG. 8: XRPD spectrum of vortioxetine hydrobromide in crystalline form σ.

A first subject of the invention is a crystalline form of vortioxetine hydrobromide selected from the group comprising:
vortioxetine hydrobromide in crystalline form, defined herein as λ, having an XRPD spectrum as shown in FIG. 1, wherein the most intense peaks are found at about 4.0; 8.0: 12.0; 12.7; 15.7; 16.0; 16.4; 19.0; 20.1; 20.3±0.2° in 2θ;
vortioxetine hydrobromide in crystalline form, defined herein as ω, having an XRPD spectrum as shown in FIG. 3, wherein the most intense peaks are found at about 3.8; 11.3: 17.5; 18.7; 18.9; 19.7; 20.5; 20.6; 22.6; 23.9; 27.1; 28.4±0.2° in 2θ; and
vortioxetine hydrobromide in crystalline form, defined herein as a, having an XRPD spectrum as shown in FIG. 8, wherein the most intense peaks are found at about 3.8, 11.6, 13.0, 14.0, 14.4, 15.5, 18.2, 18.4, 19.2, 20.0, 20.2, 21.0, 21.4, 22.3, 23.4, 23.8, 27.0 and 28.2±0.1° in 2θ.

Figure 2:
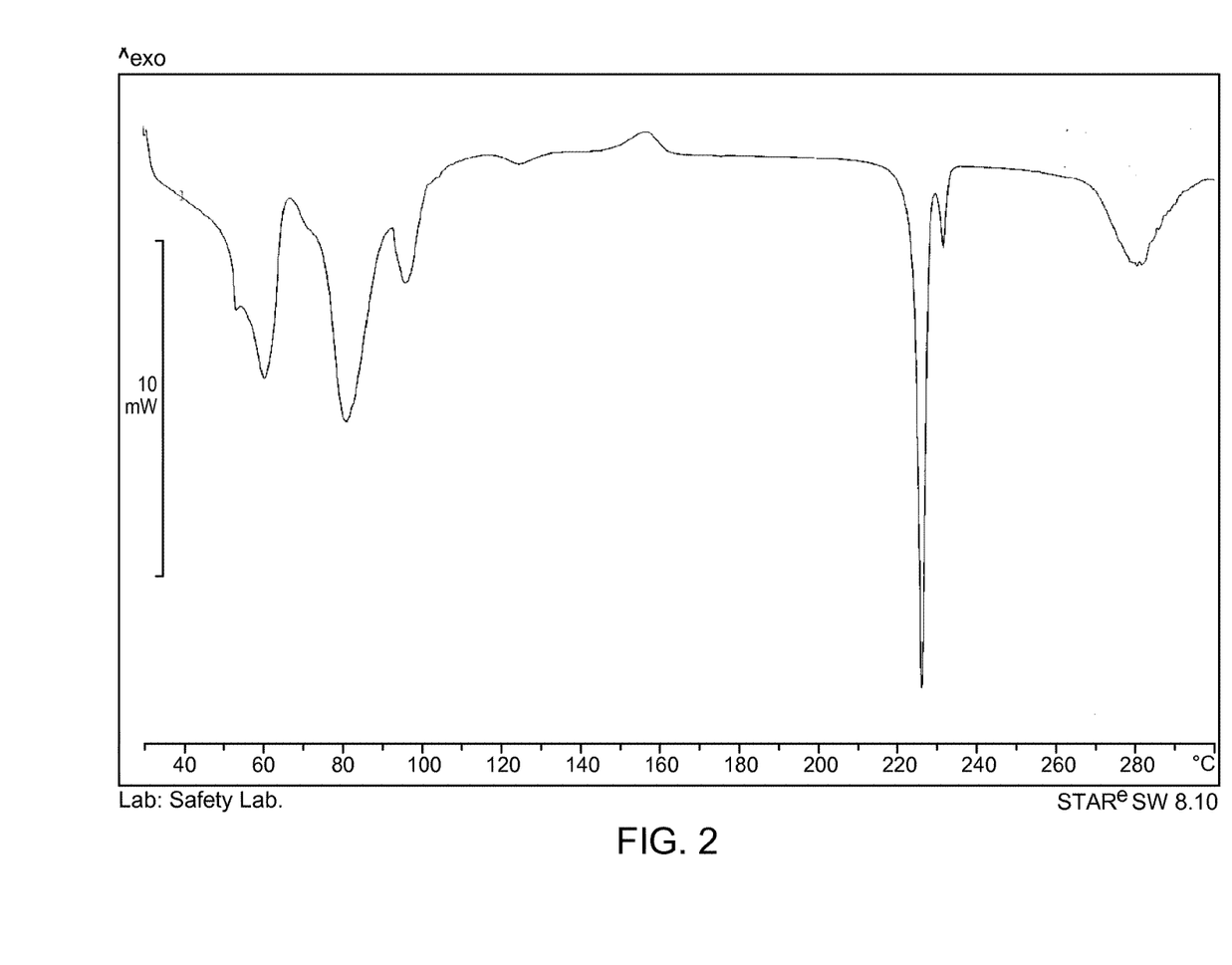
FIG. 2: DSC pattern of vortioxetine hydrobromide in crystalline form λ.

Vortioxetine hydrobromide in crystalline form λ, as defined above, is further characterised by a DSC pattern as shown in FIG. 2.

Figure 4:
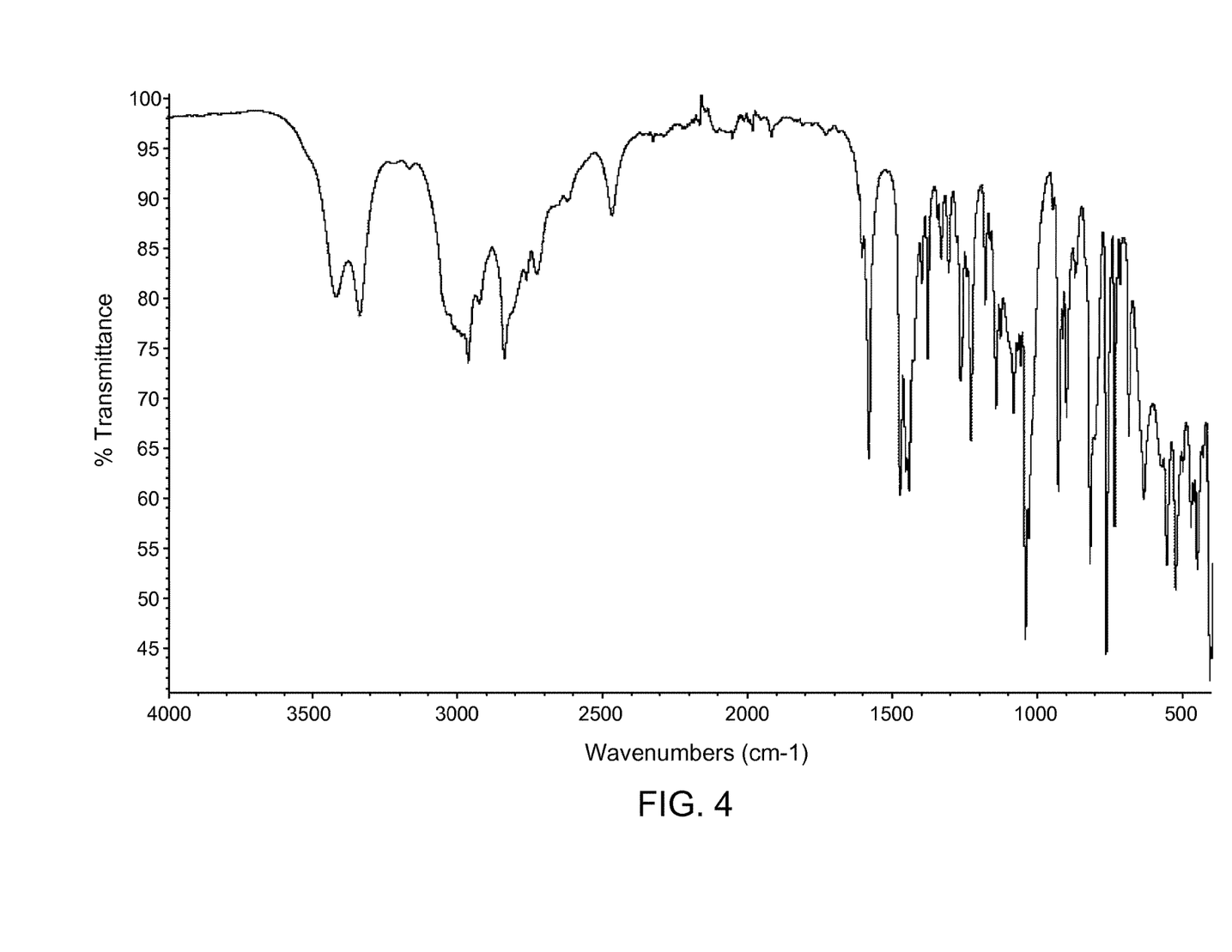
FIG. 4: FTIR spectrum of vortioxetine hydrobromide in crystalline form ω.
Figure 5:
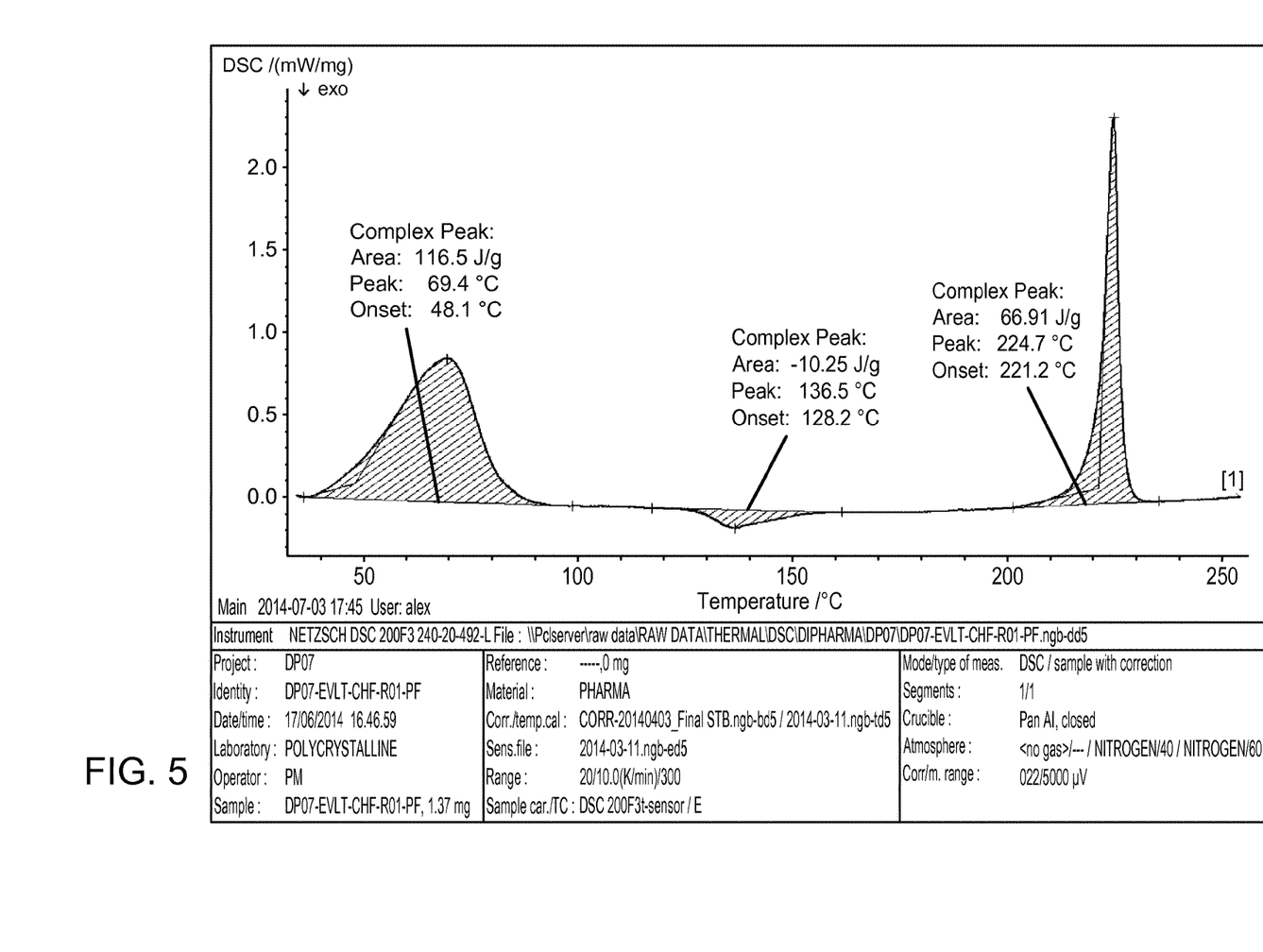
FIG. 5: DSC pattern of vortioxetine hydrobromide in crystalline form ω.

Vortioxetine hydrobromide in crystalline form ω is further characterised by an FTIR spectrum as shown in FIG. 4 and a DSC pattern as shown in FIG. 5.

According to water content analysis, vortioxetine hydrobromide in crystalline form λ, obtained according to the invention, is a hydrated form of vortioxetine hydrobromide, wherein the molar ratio between vortioxetine hydrobromide and water typically ranges between about 1:1.2 and 1:2, and is preferably around 1:1.5.

According to water content analysis, vortioxetine hydrobromide in crystalline form ω, obtained according to the invention, is a hydrated form of vortioxetine hydrobromide, wherein the molar ratio between vortioxetine hydrobromide and water typically ranges between about 0.8:1.2 and 1.2:0.8, and is preferably around 1:1.

According to water content analysis, vortioxetine hydrobromide in crystalline form σ, obtained according to the invention, has a water content comprised between about 0 and 1% w/w, preferably between about 0 and 0.5% w/w and it is therefore a substantially anhydrous crystalline form.

Figure 6:
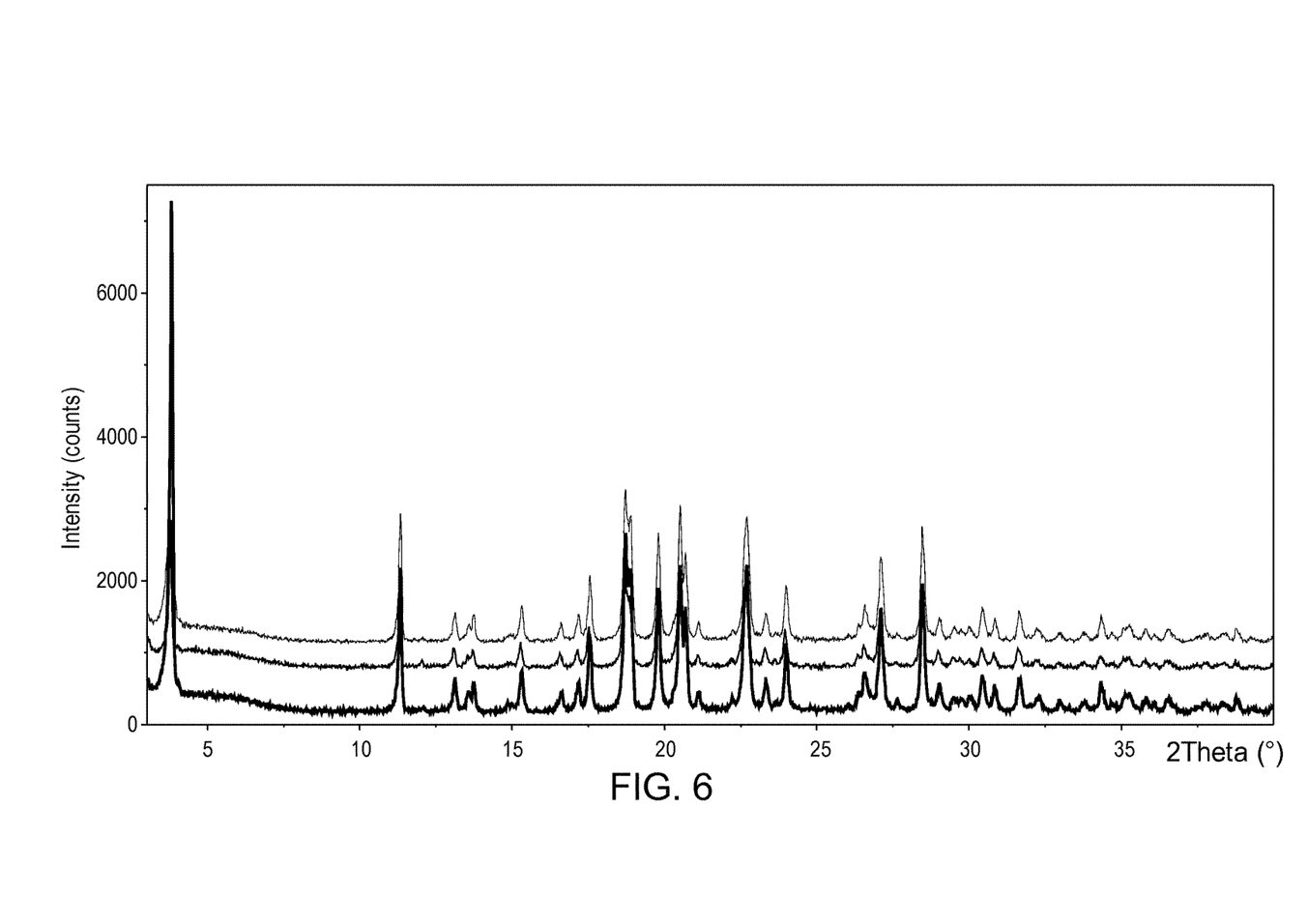
FIG. 6: Comparison of XRPD spectra of a sample of vortioxetine hydrobromide in crystalline form ω, as defined herein, freshly prepared (top line), after the same sample of vortioxetine hydrobromide in crystalline form ω has been kept at low temperature (4° C.) for 24 hours (middle line), and after the sample has been kept at room temperature for 24 hours (bottom line).
Figure 7:
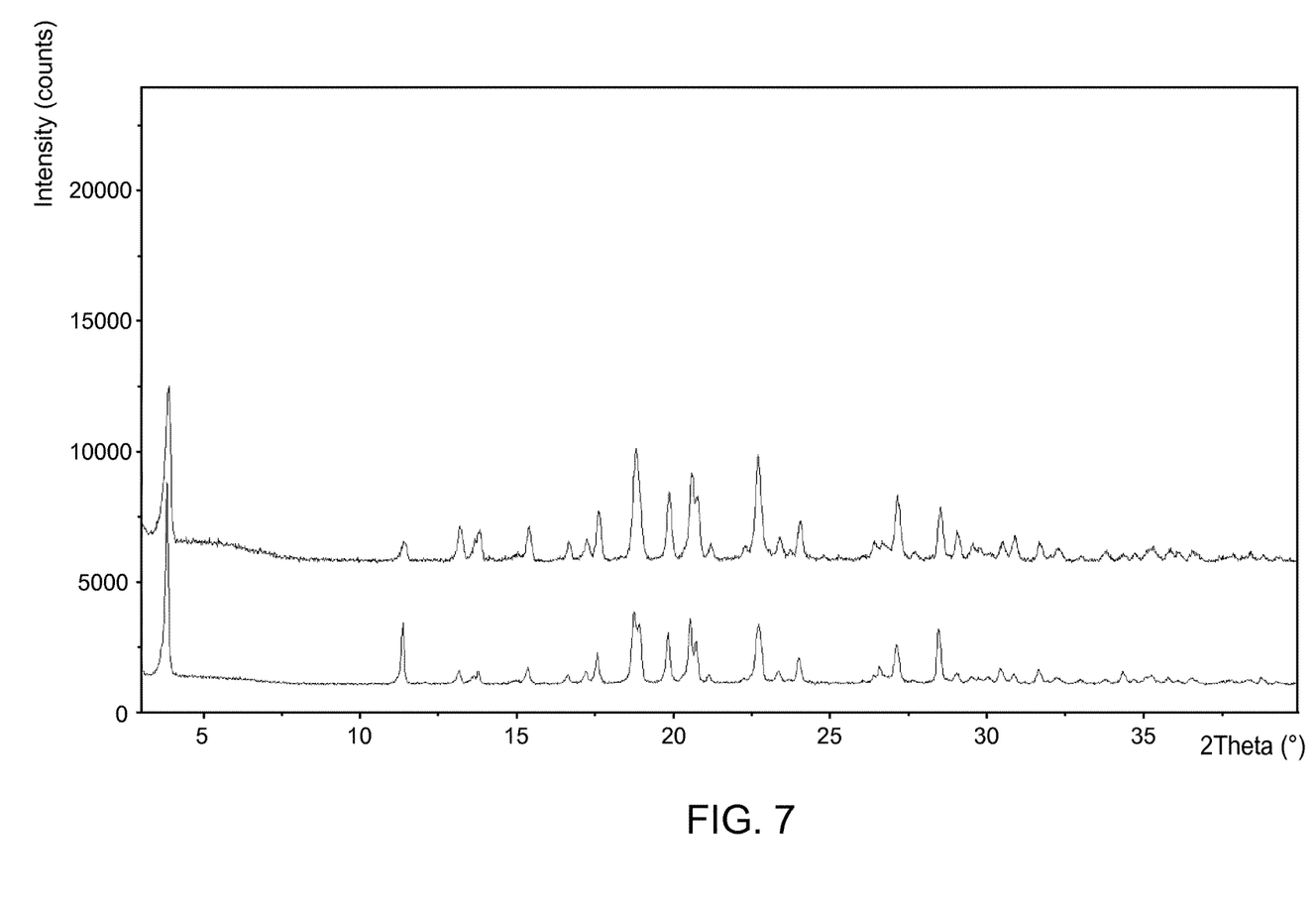
FIG. 7: Comparison of XRPD spectra of a sample of vortioxetine hydrobromide in crystalline form ω, as defined herein, freshly prepared (bottom line), and the same sample analysed after 7 days, kept at a temperature of 25° C. and 60% relative humidity (RH) (top line).

Surprisingly, the inventors of the present application have found that the polymorph ω of the invention keeps its crystalline form, even in the presence of moisture, as it can be appreciated by the XRPD spectra of FIGS. 6 and 7. This characteristic of the polymorph ω of the invention makes it more stable than other already known crystalline forms of Vortioxetine hydrobromide and enables the storage, even for prolonged time periods, of the pharmaceutical formulations incorporating it as active pharmaceutical ingredient.

Another subject of the present invention is a process for the preparation of vortioxetine hydrobromide in crystalline form λ, as defined herein, comprising:
formation of a solution of vortioxetine hydrobromide in a chlorinated solvent;
the addition of water to the resulting solution to obtain a biphasic system followed by optional cooling of the mixture to obtain a precipitate;
recovery of vortioxetine hydrobromide in crystalline form λ from the resulting dispersion;
wherein the ratio between vortioxetine hydrobromide and the chlorinated solvent in the starting solution ranges between about 100/1 mg/ml and 5/1 mg/mL, and the ratio between vortioxetine hydrobromide and the water added to the solution ranges between about 1000/1 mg/ml and about 20/1 mg/ml.

The vortioxetine hydrobromide used as starting material can be in any form, whether crystalline or non-crystalline, anhydrous, hydrated or solvated. The term "hydrated" means a form with any degree of hydration. Vortioxetine hydrobromide is typically used in alpha, beta or gamma form, as disclosed in WO 2007/144005, or in monohydrate form as known from WO 2014/044721.

A solution of vortioxetine hydrobromide is typically formed at a temperature ranging between about 10° C. and 35° C., preferably around 20-25° C.

A chlorinated solvent according to the present invention can, for example, be selected from the group comprising dichloromethane, chloroform or a mixture of said solvents. The solvent is preferably chloroform.

The ratio between vortioxetine hydrobromide and the chlorinated solvent in the starting solution typically ranges between about 20/1 mg/ml and 7/1 mg/ml, and is more preferably around 10/1 mg/ml.

The ratio between vortioxetine hydrobromide and the water added to the solution preferably ranges between about 200/1 mg/ml and 50/1 mg/ml, and is more preferably around 100/1 mg/ml.

The mixture can be cooled to a temperature ranging between about −5° C. and 15° C., preferably between about −5° C. and 5° C., and more preferably around 0° C.

Vortioxetine hydrobromide in crystalline form λ can be recovered by concentrating the resulting dispersion by methods known to the skilled person, for instance by filtration and/or centrifugation.

The vortioxetine hydrobromide in crystalline form λ thus obtained, besides as an active pharmaceutical ingredient, can be advantageously used to prepare vortioxetine hydrobromide in crystalline form ω.

A further subject of the present invention is therefore the use of vortioxetine hydrobromide in crystalline form λ to prepare vortioxetine hydrobromide in crystalline form ω, as defined above.

A subject of the present invention is therefore a process for the preparation of vortioxetine hydrobromide in crystalline form ω, comprising drying of crystalline form λ of vortioxetine hydrobromide.

Drying, typically stove drying, can be performed at a temperature ranging between about 20° C. and about 40° C., preferably at about 30° C., typically under vacuum and for a time ranging between about 1 hour and about 8 hours, preferably for about 4 hours.

Another subject of the present invention is a process for the preparation of vortioxetine hydrobromide in crystalline form ω, as defined herein, comprising:
  formation of a solution of vortioxetine hydrobromide in a chlorinated solvent;
  removal of the solvent from the resulting solution at a temperature not exceeding 20° C. and recovery of the vortioxetine hydrobromide in crystalline form ω thus obtained.

The vortioxetine hydrobromide used as starting material can be in any form, whether crystalline or non-crystalline, anhydrous, hydrated or solvated. The term "hydrated" means a form with any degree of hydration. Vortioxetine hydrobromide is typically used in alpha, beta or gamma form, as disclosed in WO 2007/144005, or in monohydrate form as known from WO 2014/044721.

Preferably, vortioxetine hydrobromide used as starting material is vortioxetine hydrobromide in monohydrate form.

A solution of vortioxetine hydrobromide is typically formed at a temperature ranging between about 10° C. and 35° C., preferably around 25-27° C.

A chlorinated solvent can be, for example, as previously defined or a mixture of said chlorinated solvents. The chlorinated solvent is preferably chloroform.

The ratio between vortioxetine hydrobromide and the chlorinated solvent in the starting solution typically ranges between about 20/1 mg/ml and 5/1 mg/mL, and is preferably around 10/1 mg/ml.

The solvent is typically removed by evaporation, for example using the "Reaction block evaporator" instrumentation supplied by JKem Scientific, set to the temperature of 8° C. and fluxing nitrogen on each vial.

The chlorinated solvent can be removed in a time ranging between about 1 and about 4 days, preferably in about 3 days.

The solvent is typically removed from the solution at a temperature not exceeding 20° C., preferably between about 2 and 15° C., more preferably around 8° C.

Another subject of the present invention is a process for the preparation of vortioxetine hydrobromide in crystalline form ω, as defined herein, comprising:
  formation of a solution of vortioxetine hydrobromide in a chlorinated solvent;
  the addition of water to the resulting solution to obtain a biphasic system followed by optional cooling to obtain a precipitate;
  recovery of vortioxetine hydrobromide in crystalline form ω from the resulting dispersion;
  wherein the ratio between vortioxetine hydrobromide and the chlorinated solvent in the starting solution ranges between about 1000/1 and 10/1 mg/mL and the ratio between vortioxetine hydrobromide and the water added to the solution ranges between about 3000/1 and 100/1 mg/mL.

A chlorinated solvent can be a solvent as defined above, preferably chloroform.

The ratio between vortioxetine hydrobromide and the chlorinated solvent in the starting solution typically ranges between about 200/1 mg/ml and 50/1 mg/mL, and is more preferably around 100/1 mg/ml.

The ratio between vortioxetine hydrobromide and water preferably ranges between about 2000/1 mg/ml and 500/1 mg/ml, and is more preferably around 1000/1 mg/ml.

The solution can be cooled to a temperature ranging between about −15° C. and 15° C., preferably between about −5° C. and 5° C., and more preferably around 0° C.

Vortioxetine hydrobromide in crystalline form ω can be recovered by concentrating the resulting dispersion by methods known to the skilled person, filtration and/or centrifugation.

Another subject of the present invention is a process for the preparation of vortioxetine hydrobromide in crystalline form ω, as defined herein, comprising:
  formation of a solution of vortioxetine base in an organic solvent;
  optional addition of water to the organic solution thus obtained;
  treatment of the mixture thus obtained with hydrobromic acid to obtain a precipitate;
  recovery of the vortioxetine hydrobromide in crystalline form ω thus obtained.

The vortioxetine base used as starting material can be any known form of vortioxetine base, either crystalline or non-crystalline, or crude vortioxetine base.

The vortioxetine base used as starting material is typically vortioxetine as obtainable according to WO 03/029232 (example 1e) or a vortioxetine base in crystalline form as disclosed in WO 2007/144005.

An organic solvent is typically an organic solvent immiscible with water, such as an aprotic apolar solvent, typically a hydrocarbon selected from hexane, heptane, toluene or xylene, preferably toluene; a chlorinated solvent, such as dichloromethane or chloroform; an ester solvent such as ethyl acetate or isopropyl acetate, an ether solvent, typically tert-butyl methyl ether or tetrahydrofuran; or a ketone, such as methyl ethyl ketone or tert-butyl methyl ketone. An organic solvent immiscible with water is preferably toluene.

The ratio between vortioxetine free base and the organic solvent in the organic solution typically ranges between about 1000/1 and 10/1 mg/mL, preferably between 100/1 mg/ml and 20/1 mg/ml, and more preferably around 20/1 mg/ml.

The hydrobromic acid used to treat the mixture is, for example, hydrobromic acid in aqueous solution, preferably 48% aqueous hydrobromic acid.

The mixture is typically treated with hydrobromic acid by dripping aqueous hydrobromic acid into the mixture in a time ranging between a few minutes and two hours.

The vortioxetine hydrobromide in crystalline form ω thus obtained can be recovered by known methods, such as filtration or centrifugation.

Another subject of the present invention is a process for the preparation of vortioxetine hydrobromide in crystalline form a, as defined herein, comprising drying crystalline form ω of vortioxetine hydrobromide.

Drying, typically stove drying or air-drying, can be performed at a temperature ranging between about 20° C. and about 100° C., preferably by stove-drying at about 40° C. under vacuum or by air-drying at 90° C. and for a time ranging between about 1 hour and about 24 hours, typically for about 15 hours.

It has also surprisingly been found that forming vortioxetine hydrobromide crystalline form λ, ω and/or σ, by starting from any form of vortioxetine base, or a pharmaceutically acceptable salt thereof, having a chemical purity equal to or lower than 98.1% calculated as Area % (A %) by HPLC, then vortioxetine base or a salt thereof having a purity exceeding 99.5% can be obtained.

A further subject of the invention is therefore a process for the purification of vortioxetine or a pharmaceutically acceptable salt thereof, in particular the hydrobromide salt, comprising the formation of vortioxetine hydrobromide in crystalline form λ, ω and/or σ.

As demonstrated by FIGS. 6 and 7, vortioxetine hydrobromide in crystalline form ω is stable from both the physical and the chemical standpoint. Said crystalline form of vortioxetine hydrobromide, under standard pressure, temperature and humidity conditions, is stable in that it does not chemically degrade and is not converted to other known crystalline forms of vortioxetine hydrobromide.

Said crystalline form ω is, in particular, not hygroscopic under standard storage conditions, and is therefore particularly suitable for use in pharmaceutical technology.

It has also surprisingly been found that said crystalline forms λ, ω and/or σ can be advantageously used to prepare another form of commercially available vortioxetine hydrobromide, in particular a crystalline form thereof. A subject of the invention is therefore the use of vortioxetine hydrobromide in crystalline form λ, ω and/or σ, as intermediate useful for preparing another form of vortioxetine hydrobromide, in particular a commercially available crystalline form thereof.

Another subject of the invention is vortioxetine hydrobromide in crystalline form ω, which is particularly stable from the physicochemical standpoint, according to the process described above.

The chemical purity of vortioxetine hydrobromide in crystalline form λ, ω and σ obtained by the process according to the invention, evaluated by HPLC analysis, is equal to or greater than 98%, and preferably equal to or greater than 99.5%.

A further subject of the invention is a pharmaceutical composition comprising vortioxetine hydrobromide in at least one of crystalline forms λ, ω or σ as defined above, as active ingredient, and a pharmaceutically acceptable excipient and/or carrier.

Said pharmaceutical composition can be prepared in a pharmaceutical form by known methods. The dose of active ingredient present in said composition can be that commonly used in clinical practice for vortioxetine hydrobromide, as reported above.

A further subject of the invention is vortioxetine hydrobromide in crystalline form λ, ω and/or σ for use as a medicament which is particularly useful in the treatment of depression.

A further subject of the invention is the use of vortioxetine hydrobromide in crystalline form λ, ω and/or σ to prepare a medicament which is particularly useful in the treatment of depression.

A further subject of the invention is therefore a method of treating a human being who need an antidepressant drug for the prevention and treatment of depressive states, comprising the administration to said human being of vortioxetine hydrobromide in crystalline form λ, ω and/or σ.

The following examples further illustrate the invention.

EXAMPLE 1

Preparation of Vortioxetine Hydrobromide in Crystalline Form λ

Vortioxetine (0.6 g, 1.58.10-3 mol) is dissolved in $CHCl_3$ (60 ml) in a 100 ml Erlenmeyer flask and filtered through a porous septum. Water (6 ml) is added and the solution is left under stirring for 24 hours at about 0° C., not in an inert atmosphere. During this period the temperature gradually rises, and the solution is concentrated to about half its volume. The solution is concentrated with nitrogen flow to residue, and taken up with 5 ml of water. The suspended solid is filtered and, when analysed with XRPD, as shown in FIG. 1, presents the most intense peaks at about 4.0; 8.0: 12.0; 12.7; 15.7; 16.0; 16.4; 19.0; 20.1; 20.3±0.2° in 2θ, with a DSC pattern as shown in FIG. 2, thus proving to be a novel hydrate polymorph (KF=7.02%), defined herein as vortioxetine hydrobromide in crystalline form λ.

EXAMPLE 2

Preparation of Vortioxetine Hydrobromide in Crystalline Form ω from Crystalline Form λ

Crystalline form λ prepared according to Example 1 can be converted to crystalline form ω by maintaining the crystalline solid under vacuum at room temperature for about 14 days or maintaining it in a stove under vacuum for about two hours at the temperature of 40° C. Said crystalline form ω thus obtained presents an XRPD spectrum as shown in FIG. 3, wherein the most intense peaks are found at about 3.8; 11.3: 17.5; 18.7; 18.9; 19.7; 20.5; 20.6; 22.6; 23.9; 27.1; 28.4±0.2° in 2θ; said crystalline form of vortioxetine hydrobromide presents a HPLC purity calculated as A % of about 99.6%. Said crystalline form also presents an FTIR spectrum as shown in FIG. 4 and a DSC pattern as shown in FIG. 5.

EXAMPLE 3

Preparation of Vortioxetine Hydrobromide in Crystalline Form ω

30 mg of vortioxetine hydrobromide in monohydrate form is dissolved in 3 mL of chloroform. The solution is maintained under stirring for about an hour at a temperature of about 25° C. The clear solution is filtered through 0.45 μm Whatman filters and left to evaporate at low temperature (8° C.) in the "Reaction block evaporator" supplied by JKem Scientific. After three days, a dark yellow crystalline solid is recovered which has an XRPD spectrum as shown in FIG. 3, wherein the most intense peaks are found at about 3.8; 11.3: 17.5; 18.7; 18.9; 19.7; 20.5; 20.6; 22.6; 23.9; 27.1; 28.4±0.2° in 2θ; said crystalline form of vortioxetine hydrobromide presents a HPLC purity calculated as A % of about 99.6%. Said crystalline form also presents an FTIR spectrum as shown in FIG. 4 and a DSC pattern as shown in FIG. 5.

EXAMPLE 4

Preparation of Vortioxetine Hydrobromide in Crystalline Form ω

Vortioxetine hydrobromide (1.5 g, 3.96·10$^{-3}$ mol) is dissolved in CHCl$_3$ (15 ml) in a 50 ml Erlenmeyer flask, and the resulting solution is filtered through a porous septum. The filtered solution is treated with water (1.5 ml), and the biphasic system thus obtained is maintained under stirring for 24 hours at about 0° C. The biphasic system is then maintained at the same temperature and a nitrogen flow is bubbled through the liquid phase until a residue is obtained, which is taken up with water (5 ml). The suspended solid is filtered and air-dried for two hours at room temperature.

Said crystalline form ω thus obtained presents an XRPD spectrum as shown in FIG. 3, wherein the most intense peaks are found at about 3.8; 11.3: 17.5; 18.7; 18.9; 19.7; 20.5; 20.6; 22.6; 23.9; 27.1; 28.4±0.2° in 2θ; said crystalline form of vortioxetine hydrobromide presents a HPLC purity calculated as A % of about 99.6%. Said crystalline form presents an FTIR spectrum as shown in FIG. 4 and a DSC pattern as shown in FIG. 5.

EXAMPLE 5

Preparation of Vortioxetine Hydrobromide in Crystalline Form ω from Vortioxetine Base Vortioxetine hydrobromide (1.0 g, 2.64 mmol, HPLC purity 98.01%) is suspended in toluene (20 ml) under nitrogen in a 100 ml four-necked flask equipped with magnetic stirrer, thermometer and condenser, and water (20 ml) and about 0.5 ml of 30% NaOH are added. The mixture is heated to about 80° C., and the phases are then separated at the same temperature. The organic phase is then treated with water (20 ml), maintaining the temperature at 80° C., and the biphasic system is treated with 48% HBr (0.3 ml). The phases are separated and the organic phase is further extracted hot with water. The combined aqueous phases are treated with 30% NaOH to pH 11, and extracted hot several times with toluene.

The combined organic phases are partly concentrated at low pressure to about 16 ml of organic solution, and treated at about 20° C. with water (2 ml). The biphasic system is treated with 48% HBr (0.3 ml), and the mixture is maintained under stirring for two hours at about 20° C. The crystallised solid is filtered, washed with water and stove-dried for 4 hours at 40° C. under vacuum. 1.0 g of vortioxetine hydrobromide hydrate form ω, with KF=4.53 and HPLC purity in A % of 99.82, is obtained.

Said crystalline form ω thus obtained presents an XRPD spectrum as shown in FIG. 3, wherein the most intense peaks are found at about 3.8; 11.3: 17.5; 18.7; 18.9; 19.7; 20.5; 20.6; 22.6; 23.9; 27.1; 28.4±0.2° in 2θ; said crystalline form of vortioxetine hydrobromide presents a HPLC purity calculated as A % of about 99.6%. Said crystalline form also presents an FTIR spectrum as shown in FIG. 4, and a DSC pattern as shown in FIG. 5.

EXAMPLE 6

Preparation of Vortioxetine Hydrobromide in Crystalline Form σ

Vortioxetine hydrobromide in crystalline form ω, as obtained according to example 5, is stove-dried under vacuum at 40° C. for 15 hours.

Vortioxetine hydrobromide in crystalline form σ is obtained.

Said crystalline form σ thus obtained presents an XRPD spectrum as shown in FIG. 8, wherein the most intense peaks are found at about 3.8, 11.6, 13.0, 14.0, 14.4, 15.5, 18.2, 18.4, 19.2, 20.0, 20.2, 21.0, 21.4, 22.3, 23.4, 23.8, 27.0 and 28.2±0.1° in 2θ; said crystalline form of vortioxetine hydrobromide presents a KF=0.4% and a HPLC purity calculated as A % of about 99.7%.

EXAMPLE 7

Preparation of Vortioxetine Hydrobromide in Crystalline Form σ

Vortioxetine hydrobromide in crystalline form ω, as obtained according to example 5, is air-dried at 90° C.

Vortioxetine hydrobromide in crystalline form σ is obtained.

Said crystalline form σ thus obtained presents an XRPD spectrum as shown in FIG. 8, wherein the most intense peaks are found at about 3.8, 11.6, 13.0, 14.0, 14.4, 15.5, 18.2, 18.4, 19.2, 20.0, 20.2, 21.0, 21.4, 22.3, 23.4, 23.8, 27.0 and 28.2±0.1° in 2θ; said crystalline form of vortioxetine hydrobromide presents a KF=0.4% and a HPLC purity calculated as A % of about 99.7%.

The invention claimed is:

1. A crystalline form of vortioxetine hydrobromide selected from the group comprising:

vortioxetine hydrobromide in crystalline form, herein defined as λ, having an XRPD spectrum as shown in FIG. 1, having the most intense peaks falling at about 4.0; 8.0: 12.0; 12.7; 15.7; 16.0; 16.4; 19.0; 20.1; 20.3±0.2° in 2θ; and vortioxetine hydrobromide in crystalline form, herein defined as ω, having an XRPD spectrum as reported in FIG. 3, having the most intense peaks falling at about 3.8; 11.3: 17.5; 18.7; 18.9; 19.7; 20.5; 20.6; 22.6; 23.9; 27.1; 28.4±0.2° in 2θ; and vortioxetine hydrobromide in crystalline form, defined herein as σ, having an XRPD spectrum as shown in FIG. 8, wherein the most intense peaks are found at about 3.8, 11.6, 13.0, 14.0, 14.4, 15.5, 18.2, 18.4, 19.2, 20.0, 20.2, 21.0, 21.4, 22.3, 23.4, 23.8, 27.0 and 28.2+0.1° in 2θ.

2. A crystalline form λ, as defined in claim 1, which shows a DSC pattern as reported in FIG. 2; or a crystalline form ω, as defined in claim 1, having an FT-IR spectrum as reported in FIG. 4, and a DSC pattern as reported in FIG. 5.

3. A pharmaceutical composition comprising vortioxetine hydrobromide in at least one of the crystalline forms λ, ω and/or σ as defined in claim 1, as active pharmaceutical ingredient, and a pharmaceutically acceptable excipient and/or carrier.

4. Vortioxetine hydrobromide in crystalline form λ, ω and/or σ, as defined in claim 1, in combination with an excipient and/or carrier suitable for use with an antidepressant.

* * * * *